US012564884B2

(12) United States Patent
Lathabai et al.

(10) Patent No.: US 12,564,884 B2
(45) Date of Patent: Mar. 3, 2026

(54) IMPLANTABLE OBJECTS FABRICATED BY ADDITIVE MANUFACTURING AND METHODS OF FABRICATING THE SAME

(71) Applicant: FLEX MEMORY VENTURES PTY LTD, Burwood (AU)

(72) Inventors: Srinivasarao Lathabai, Wollongong (AU); Meltem Yesim Gozukara, Acton (AU); David James Bell Ritchie, Acton (AU); Kishore Venkatesan, Acton (AU)

(73) Assignee: FLEX MEMORY VENTURES PTY LTD, Burwood (AU)

( * ) Notice: Subject to any disclaimer, the term of this patent is extended or adjusted under 35 U.S.C. 154(b) by 946 days.

(21) Appl. No.: 17/431,042

(22) PCT Filed: Feb. 13, 2020

(86) PCT No.: PCT/AU2020/050122
§ 371 (c)(1),
(2) Date: Aug. 13, 2021

(87) PCT Pub. No.: WO2020/163915
PCT Pub. Date: Aug. 20, 2020

(65) Prior Publication Data
US 2022/0126368 A1      Apr. 28, 2022

(30) Foreign Application Priority Data
Feb. 13, 2019    (AU) ................................ 2019900458

(51) Int. Cl.
B22F 10/62          (2021.01)
A61F 2/28           (2006.01)
(Continued)

(52) U.S. Cl.
CPC ................ *B22F 10/62* (2021.01); *A61F 2/28* (2013.01); *A61F 2/89* (2013.01); *B22F 10/28* (2021.01);
(Continued)

(58) Field of Classification Search
CPC ........ B22F 10/28; B22F 10/36; B22F 10/364; B22F 10/366; B22F 10/47; B22F 10/62;
(Continued)

(56) References Cited

U.S. PATENT DOCUMENTS 6,375,826 B1      4/2002  Wang et al.
2006/0198750 A1   9/2006  Furst et al.
(Continued)

FOREIGN PATENT DOCUMENTS

CN      107802886 A      3/2018
CN      108403256        8/2018

OTHER PUBLICATIONS

International Search Report of PCT/AU2020/050122, Mar. 18, 2020, 7 pp.
(Continued)

*Primary Examiner* — Moshe Wilensky
(74) *Attorney, Agent, or Firm* — WOMBLE BOND DICKINSON (US) LLP

(57) ABSTRACT

An implantable object (1000') and a method (100) of fabricating an implantable object is disclosed. The method (100) comprises melting a powder (210) comprising at least nickel and titanium with an energy source (220) and iteratively forming a plurality of stacked metallic layers (330) from the melted powder using an additive manufacturing technique. The implantable object is biased to expand from a first configuration (501) to a second configuration (502) when at or above a transformation temperature.

17 Claims, 8 Drawing Sheets

Melting a powder comprising at least nickel and titanium with an energy source
110

Iteratively forming a plurality of stacked metallic layers from the melted powder using additive manufacturing
120

Heat treating the plurality of stacked metallic layers
130

Removing at least a portion of an outer surface of the stacked metallic layers
140

(51) Int. Cl.

| | |
|---|---|
| *A61F 2/89* | (2013.01) |
| *B22F 10/28* | (2021.01) |
| *B22F 10/36* | (2021.01) |
| *B22F 10/366* | (2021.01) |
| *B22F 10/47* | (2021.01) |
| *B22F 10/68* | (2021.01) |
| *B22F 12/47* | (2021.01) |
| *B33Y 10/00* | (2015.01) |
| *B33Y 40/20* | (2020.01) |
| *B33Y 80/00* | (2015.01) |
| *A61F 2/915* | (2013.01) |
| *B22F 10/364* | (2021.01) |
| *B22F 10/64* | (2021.01) |
| *B22F 12/41* | (2021.01) |

(52) U.S. Cl.
CPC ............ *B22F 10/36* (2021.01); *B22F 10/366* (2021.01); *B22F 10/47* (2021.01); *B22F 10/68* (2021.01); *B22F 12/47* (2021.01); *B33Y 10/00* (2014.12); *B33Y 40/20* (2020.01); *B33Y 80/00* (2014.12); *A61F 2002/91575* (2013.01); *A61F 2210/0014* (2013.01); *A61F 2240/001* (2013.01); *A61F 2310/00023* (2013.01); *B22F 10/364* (2021.01); *B22F 10/64* (2021.01); *B22F 12/41* (2021.01); *B22F 2301/205* (2013.01)

(58) Field of Classification Search
CPC .......... B22F 10/64; B22F 10/68; B22F 12/41; B22F 12/47; B22F 3/1115; B22F 5/10; B22F 2301/15; A61F 2/28; A61F 2/89; A61F 2/3094; A61F 2/915; A61F 2/02; A61F 2210/0014; A61F 2240/001; A61F 2310/00023; A61F 2002/91575; A61F 2002/30985; A61F 2002/30092; B33Y 10/00; B33Y 40/20; B33Y 80/00; C22C 1/0458; C22C 1/0433
See application file for complete search history.

(56) References Cited

U.S. PATENT DOCUMENTS

| | | | |
|---|---|---|---|
| 2008/0121530 A1 | 5/2008 | Piesslinger-Schweiger et al. | |
| 2008/0131479 A1 | 6/2008 | Weber et al. | |
| 2010/0070022 A1 | 3/2010 | Kuehling | |
| 2015/0132173 A1 | 5/2015 | Bruck et al. | |
| 2015/0306667 A1* | 10/2015 | Yao ..................... | B23K 26/342 |
| | | | 419/54 |
| 2016/0052162 A1* | 2/2016 | Colin ................ | A61C 13/0018 |
| | | | 425/162 |
| 2017/0014235 A1 | 1/2017 | Jones et al. | |

OTHER PUBLICATIONS

International Written Opinion of PCT/AU2020/050122, Mar. 18, 2020, 4 pp.

* cited by examiner

Melting a powder comprising at least nickel and titanium
with an energy source
110

Iteratively forming a plurality of stacked metallic layers
from the melted powder using additive manufacturing
120

Heat treating the plurality of stacked metallic layers
130

Removing at least a portion of an outer surface of the
stacked metallic layers
140

1000

1020

6 mm

1000'

1040

6 mm

IMPLANTABLE OBJECTS FABRICATED BY ADDITIVE MANUFACTURING AND METHODS OF FABRICATING THE SAME

CROSS-REFERENCE TO RELATED APPLICATION(S)

This application is a U.S. National Phase Patent Application of PCT/AU2020/050122, filed Feb. 13, 2020, which claims priority to Australian patent application 2019900458, filed on Feb. 13, 2019, the entire content of each of which is hereby incorporated by reference.

TECHNICAL FIELD

The present invention generally relates to objects fabricated with additive manufacturing and methods for fabricating objects. More specifically but not limited to, the present invention relates to implantable objects comprising nickel-titanium alloy fabricated with additive manufacturing and methods for fabricating the same.

BACKGROUND

Nickel-titanium alloys, also known as Nitinol, may exhibit a shape memory effect and superelastic behaviour. Superelasticity (also referred to as pseudoelasticity) is reversible elastic characteristic of a material. Superelasticity includes the ability to deform elastically in a non-linear manner by as much as 10% and then recover the strain at a lower stress when the deforming stress is released. The superelastic behaviour enables Nitinol to mimic the elastic deformation behaviour of natural materials of the living body such as hair, tendon and bone. This elastic deformation behaviour is completely different from that of conventional materials such as stainless steels or cobalt-base alloys which display elastic deformations of the order of 1%, proportional with the applied stress.

However, Ni—Ti alloys are difficult to manufacture by conventional methods such as machining. Existing methods for manufacturing with Ni—Ti alloys that involve cutting or removal of material result in wastage of expensive stock material and are time consuming.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In an aspect of the invention, there is provided a method of fabricating an implantable object comprising:

melting a powder comprising at least nickel and titanium with an energy source; and iteratively forming a plurality of stacked metallic layers from the melted powder using additive manufacturing, such that the implantable object is biased to expand from a first configuration to a second configuration when at or above a transformation temperature.

The method may further comprise forming a support structure by iteratively forming a plurality of stacked support layers wherein each support layer is formed from partially melted powder. The support structures may be removable.

The support structures may be at least partially removed by pickling the implantable object.

The support structures may be at least partially removed by electro-polishing the implantable object.

An implantable object may be advantageously formed from the plurality of stacked layers. The nickel and titanium content of the powder means that the implantable object is biased to expand. This expansion advantageously enables the implantable object to provide a useful function when implanted within a patient. For example, if the implantable object is inserted into a blood vessel to act as a vascular stent, the bias to expand enables the implantable object to apply outward pressure to the inside of the blood vessel.

In some embodiments, iteratively forming the stacked metallic layers comprises iteratively changing a relative position of the energy source along a first axis and then the relative position changes along a second axis parallel to the first axis with a hatch spacing between the first axis and second axis in the range of about 30 microns to about 100 microns. The range for the hatch spacing advantageously sets the energy density of the energy source which may affect the transformation temperature. Additionally, the remelting of previously melted powder is set while ensuring that newly melted powder is connected to previously melted powder to form a continuous solid metallic layer if necessary.

In some embodiments, the relative position changes with a speed in the range of about 105 mm/s to 1245 mm/s. The speed advantageously sets the energy density of the energy source which may affect the transformation temperature.

In some embodiments, the energy source is a laser beam with a power in the range of about 55 W to less than 200 W. The power advantageously sets the energy density of the energy source which may affect the transformation temperature.

In some embodiments, the energy source has a power; and the hatch spacing, the scan speed, and the power of the laser beam are selected to produce an energy density in the range of about 50 kJ/mm$^3$ to about 90 kJ/mm$^3$. Energy densities in this range may advantageously set the transformation temperature within a desired range.

In some embodiments, melting the powder is performed while the powder is supported by a nickel-titanium alloy substrate. Supporting the powder on a nickel-titanium alloy advantageously reduces the stress in the plurality of layers as they are iteratively formed.

In some embodiments, the energy source is focused on the powder to produce molten powder such that the molten powder has a lateral dimension in the range of about 75 microns to about 200 microns. Focusing the energy to this range of lateral dimensions advantageously enables components of the implantable object to have dimensions within this range or for the components to have features sized within this range.

In some embodiments, the iterative forming of stacked layers comprises forming at least one layer of molten powder with a thickness in the range of about 20 microns to about 40 microns. Forming layers with a thickness in this range may provide a thickness that enables the layer to be melted as well as a portion of the underlying layer to advantageously join the layers together.

In some embodiments, the iterative forming of stacked layers comprises forming at least one layer with a thickness in the range of about 25 microns to about 35 microns.

In some embodiments, the transformation temperature is a finish temperature for transformation from martensite to austenite. The transformation temperature being the finish temperature from martensite to austenite may advantageously enable the implantable object to exhibit superelastic and/or shape memory effects at or above the transformation temperature.

In some embodiments, wherein the finish temperature is less than or at about human body temperature. By providing a transformation temperature less than or at about human body temperature, the implantable object may be advantageously biased to expand to the second configuration when implanted within a living human being.

In some embodiments, the finish temperature is less than about 36° C.

In some embodiments, the powder comprises at least about 56 weight % nickel. A powder comprising at least about 56 weight % nickel may advantageously compensate for excessive nickel evaporation during additive manufacturing.

In some embodiments, the implantable object is thereby formed from a shape memory alloy. Forming the implantable object from shape memory alloy advantageously enables the implantable object to exhibit superelastic and/or shape memory effects when above the transformation temperature.

In some embodiments, the implantable object is superelastic when above the transformation temperature. A superelastic implantable object may advantageously be compressed to the first configuration and resiliently biased to expand to the second configuration without excessive damage to the implantable object.

In some embodiments, the method further comprises changing the relative position according to a set of instructions to form a plurality of crowns comprising a plurality of struts, wherein adjacent crowns are connected to each other by at least one strut, and a first thickness of a first set of struts is greater than a second thickness of a second set of struts.

In some embodiments, the method further comprises removing at least a portion of the second set of struts. The method may further comprise removing the second set of struts.

In some embodiments, the method comprises removing at least a portion of the surface of the plurality of struts.

In some embodiments, the method further comprises heat treating the implantable object to lower the transformation temperature. The method may also further comprise quenching the implantable object in a liquid after heat treating.

The method may further comprise pickling the implantable object in a solution comprising hydrofluoric acid (HF) and nitric acid ($HNO_3$) for a predetermined time period.

The predetermined time period may be 15 minutes and the solution may comprise 5% HF, 30% $HNO_3$ and 65% water.

The method may further comprise electro-polishing the implantable object in a solution of sulphuric acid ($H_2SO_4$) and methanol.

The solution may comprise 10% sulphuric acid.

The electro-polishing may be performed at a voltage of 8 V.

The above method may further comprise electro-polishing the implantable object in methanesulfonic acid.

The electro-polishing may be performed at a voltage of 20 V.

In an aspect of the invention, there is provided an implantable object comprising:
    a plurality of crowns, each crown comprising a plurality of connected struts formed using additive manufacturing;
    wherein the crowns are formed by melting a powder comprising at least nickel and titanium, and the implantable object is biased to expand from a first configuration to a second configuration when at or above a transformation temperature.

In some embodiments, the transformation temperature is a finish temperature for martensite to austenite transformation.

In some embodiments, the implantable object is fabricated by any of the methods described herein.

In some embodiments, the implantable object is a stent. In some embodiments, the implantable object may comprise a first thickness of a first set of the connected struts which is greater than a second thickness of a second set of the connected struts.

In some embodiments, the implantable object is formed from a shape memory alloy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments are described in further detail below, by way of example, with reference to the accompanying drawings briefly described below. Like references refer to like features.

DESCRIPTION OF EMBODIMENTS

The shape memory effect of Ni—Ti alloys can also be exploited in applications such as stents. Coronary and peripheral stents are typically implanted into blood vessels, such as arteries, with an expandable bladder within the central lumen of the stent. Once implanted, the bladder is expanded from within the stent to thereby expand the stent to thereby dilate the blood vessel. If the transformation temperature of the alloy is less than body temperature, then a stent formed from that alloy that is implanted into a blood vessel will expand within a blood vessel without the need for an expandable bladder.

Additive Manufacturing (AM), which builds up parts by applying material precisely where it is needed, in a layer-by-layer manner based on a computer aided design (CAD) model, offers the potential to reduce material wastage and furthermore provides the ability for patient specific custom design and greater design freedom.

The resultant properties of objects fabricated with additive manufacturing (also referred to as 3D printing) may be dependent on the build parameters defining the additive manufacturing method. This is particularly important for fabrication of metallic objects as the microstructure of the resultant object can be affected by the method of fabrication which can in turn affect the mechanical properties of the object. In the case of nickel-titanium alloys (nitinol), the build parameters may also affect the temperatures at which transformation between martensitic and austenitic phases occur. These build parameters are explained using a brief explanation of relevant additive manufacturing methods below.

Figure 1:
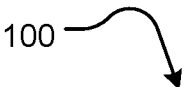
FIG. 1 is flow chart for a method of fabricating an implantable object.
Figure 1:
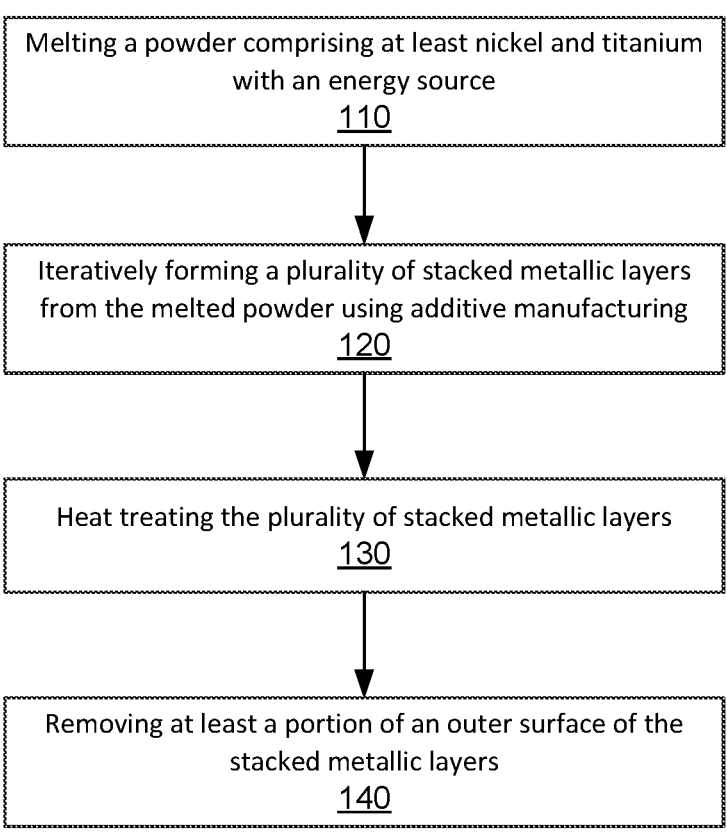
Figure 2:
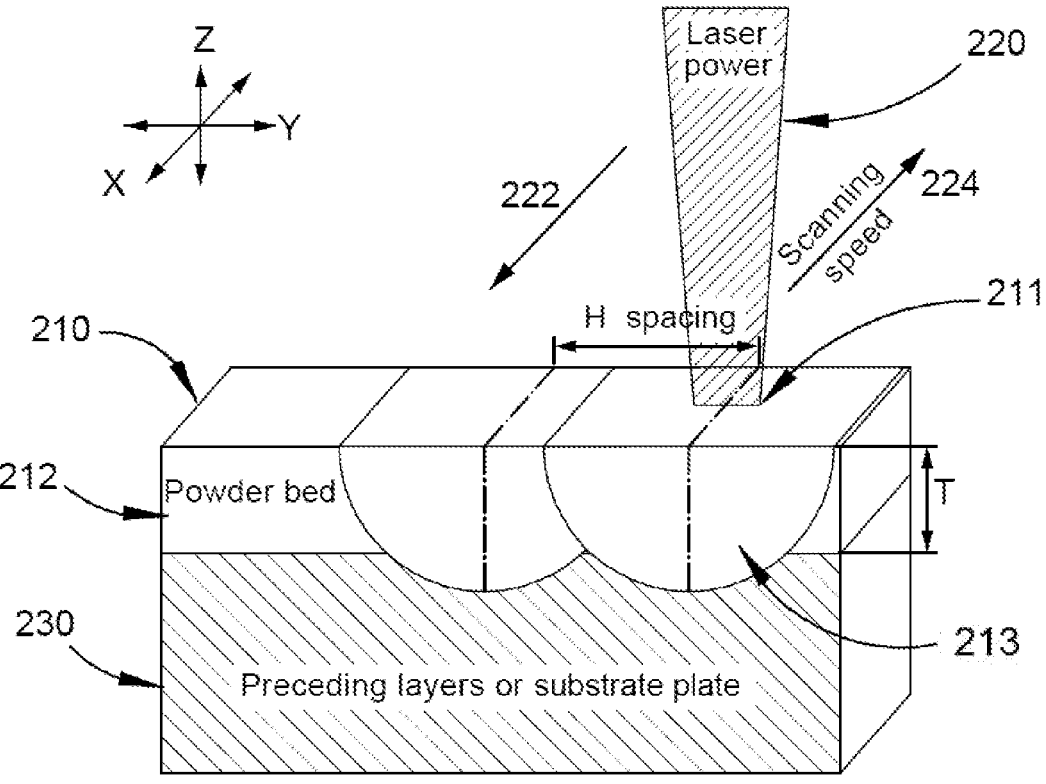
FIG. 2 is a schematic diagram illustrating a known method of additive manufacturing by selective laser melting.
Figure 3:
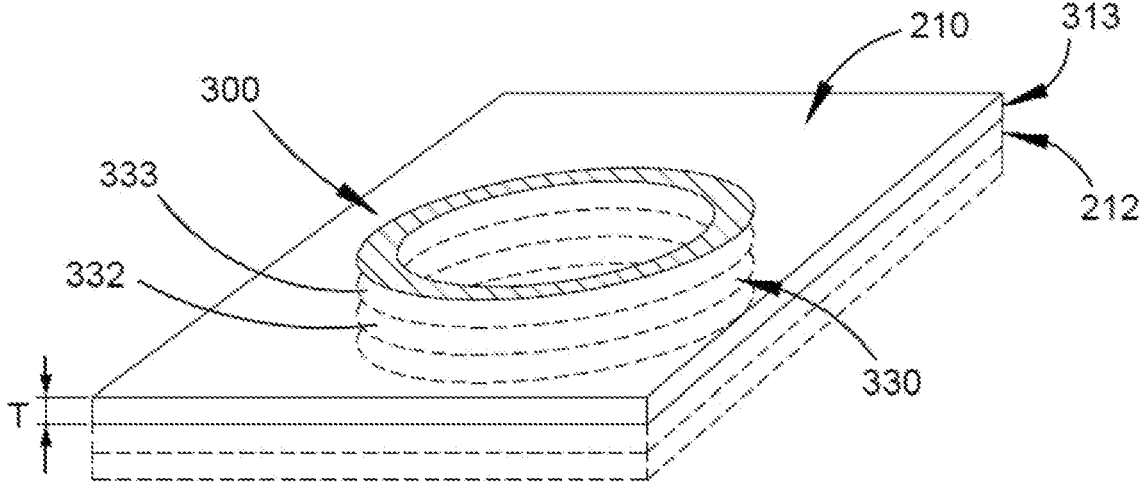
FIG. 3 is a schematic diagram of an implantable objected being fabricated with the method of FIG. 1.

Referring to FIGS. 1, 2 and 3, a method 100 of fabricating an implantable object 300 comprises melting a powder 210 comprising at least nickel and titanium with an energy source 220, at 110. The method 100 further comprises iteratively forming a plurality of stacked metallic layers 330 with additive manufacturing to thereby fabricate the object 300, at 120. In some embodiments, the powder 210 is a pre-alloyed combination of at least nickel and titanium, i.e. the powder 210 comprises particles which each comprise an alloy of at least nickel and titanium. In some embodiments, the powder 210 is a mixture of particles comprising at least nickel and particles comprising at least titanium.

The method 100 may also comprise one or more of the steps of: heat treating the implantable object 300, at 130; and removing at least a portion of the implantable object 300, at 140 to substantially smooth the surface of object 300.

Additive Manufacturing

In some embodiments, iteratively forming 120 the plurality of stacked metallic layers 330 with additive manufacturing involves directing the energy source 220 onto an area 211 of a layer 212 of powder 210 to heat and thereby melt a volume 213 of the powder 210 to produce molten powder (or a melt-pool or melted powder). The molten powder of volume 213 may, for example, have a semicircular-like cross-section. The molten volume 213 may have a smallest size dimension ('bead' dimension) along a lateral axis Y in the range of about 75 microns to about 200 microns.

The energy source 220 may, for example, be a laser beam provided by a ytterbium fibre laser at a wavelength of 1070 nm. The size of the area 211 irradiated by the laser beam may be selected to set an energy density ε for Selective Laser Melting (SLM) additive manufacturing. For example, the laser beam may be directed into a smaller area resulting in a higher energy density. The laser beam 220 may be defined by a power P which may be selected to set the energy density injected into the powder 210. Using a higher laser power may result in a higher energy density, for example, the energy density may be proportional to the power. Examples of additive manufacturing systems for SLM are the 'Concept Laser M2 Cusing' and Concept Laser Mlab systems by GE Additive.

In some embodiments, the energy source 220 may be an electron beam (not shown). The electron beam may be focused into an area 211 on the powder 210 to heat and thereby melt the powder 210 to form layer 332.

The laser beam may be focused on the area 211 to produce the molten volume 213 such that the smallest dimension of the molten volume 213 is in the range of about 75 microns to about 250 microns. The smallest dimension of the molten volume 213 may be the same as a diameter of a molten bead (not shown) formed.

The relative position between the energy source 220 and the powder 210 may be changed along a first axis X in a first direction 222 at a speed to thereby progressively melt the powder 210 along the first axis X. For example, if the energy source 220 continuously exposes (or irradiates) the powder 210 while the relative position is changed, a molten segment 214 or line of the powder 210 may be formed. The speed at which the relative position changes may be selected to set the energy density. A higher speed may result in a lower energy density, for example, the energy density may be inversely proportional to the speed. A higher speed may also result in a smaller molten volume 213 and bead dimension.

After the relative position is changed along a first axis X, the relative position may be stepped along a second axis Y by an amount defined by a hatch spacing H. The second axis Y may be orthogonal to the first axis X. After the relative position has been changed along the second axis Y, the relative position may be changed along the first axis X in a second direction 224. The second direction 224 being opposite to the first direction 222. The hatch spacing H may be selected to set the energy density. A larger hatch spacing H may result in a lower energy density, for example, the energy density may be inversely proportional to the hatch spacing H.

The hatch spacing H may be selected such that, during movement in the second direction 224 along the first axis X, there is partial remelting of the previously molten volume 213 that was formed when the relative position was changed in the first direction 222. In some embodiments, the hatch spacing H may be in the range of about 30 microns to about 100 microns. The hatch spacing H may, for example be any one of 30 microns, 50 microns, 75 microns and 100 microns. The spacing between adjacent curved tracks of movement may also be separated by a hatch spacing H.

By changing the relative position over at least one of the first axis, X, or the second axis, Y, different areas 211 of the powder 210 can be melted. Connected melted sections cool and solidify to form a connected solid. This process is repeated for each layer in the additive manufacturing process to form a plurality of stacked layers 330 that solidify into a fabricated item once cooled. The solid stacked layers 330 may comprise Ni—Ti intermetallic phases such as a Ni—Ti martensitic phase. As explained further below, selective exposure of the powder 210 to the energy source 220 (e.g. laser beam) may be used to form a plurality of unconnected solid areas 433, 434, 435 within the same powder layer 313.

In some embodiments, the relative position is simultaneously changed over the first axis X and the second axis Y such that the position changes over a curved track (e.g. contour).

Additional powder may be added over the solid layer 332 formed which is further exposed to the energy source 220 to form additional solid layer 333 and thereby iteratively form the stacked layers 330 of material. For example, the additional powder may be added as a continuous powder layer 313 over the solid layer 332 and the existing powder layer 312 (i.e. in the SLM additive manufacturing). During formation of the additional solid layer 333, the previous solid layer 332 may also be partially melted to improve bonding between the stacked layers 330.

Each of the stacked layers 330 may be iteratively formed and the object 300 may be fabricated layer-by-layer, in a bottom-up fashion, along a third axis Z that is orthogonal to the first axis X and the second axis Y. In some embodiments, the height of the powder layer 212 (and the substrate 230) is lowered to maintain the height of the uppermost layer of powder 210 along the third axis Z after the addition of additional powder over the formed solid layer 332.

Prior to irradiation from the energy source 220, the powder 210 may be deposited as a powder layer 212, 313 (or powder bed) with a layer thickness T. The layer thickness T may also be selected to set the energy density. A larger layer thickness T may result in a lower energy density. For example, the energy density may be inversely proportional to the layer thickness.

The layer thickness T may be in the range of about 20 microns to about 40 microns. In some embodiments, the layer thickness T is in the range of about 25 microns to about 35 microns. For example, the layer thickness T may be about 30 microns. The layer thickness T is in part defined by the separation between the 230 substrate (or previous powder layer 212) and a dosing chamber (not shown). The separation is typically larger than the layer thickness due to packing of the powder 210 when the powder layer 212, 213 is deposited. In some embodiments, the separation is 150% of the layer thickness T.

The melting 110 of the powder 210 and iteratively forming 120 a plurality of stacked metallic layers 330 with additive manufacturing is conducted in an inert atmosphere to reduce and/or prevent embrittlement of the stacked metallic layers 330 due to oxidation. The inert atmosphere may comprise low oxygen concentrations in the range of 0-0.4 weight percent (wt. %) O in a build chamber (not shown). The inert atmosphere may comprise an argon-rich atmosphere.

In some embodiments, the powder layer 212 is initially deposited on a nickel-titanium alloy substrate 230. The method 100 may comprise forming a first solid metallic layer 332 on the nickel-titanium alloy substrate 230. Iteratively forming 120 the plurality of stacked metallic layers 330 on a substrate 230 that comprises a nickel and titanium alloy may reduce the chances of forming a brittle reaction layer between the substrate 230 and the first metallic layer 213 which can lead to cracking in the stacked metallic layers 330.

The powder 210 may comprise generally spherical particles with a distribution of particle diameters. The powder 210 may comprise particles with a median particle diameter that is, for example, around 34 microns. The powder 210 may have a particle size distribution such that 10% of the particles have a diameter less than about 20 microns and 90% have a diameter less than about 45 microns. In some embodiments, the powder 210 comprises particles with a diameter in the range of about 10 microns to about 50 microns. The particle size distribution may, for example, be measured by analysis of laser scattering and/or diffraction by the particles.

The powder 210 may comprise at least about 54.2% by weight (wt. %) of nickel. In some embodiments, the chemical composition of powder 210 conforms to the ASTM F 2063 standard of ASTM International. The powder 210 may therefore comprise about 54.5 wt. % nickel.

In some embodiments, the powder 210 comprises about 57.0 wt. % nickel. In some embodiments, the powder 210 comprises about 56.5 wt. % nickel. The powder 210 may comprise about 56.0 wt. % nickel. The powder 210 may comprise about 55.0 wt. % nickel. The higher initial nickel concentration in the powder 210 may compensate for nickel loss during additive manufacturing fabrication as discussed further below so that the implantable object 300 has a desired concentration (e.g. at least about 54.5 wt. %) of nickel. The powder 210 may therefore comprise less than 45 wt. % titanium, for example, about 43.0 wt. %, about 43.5 wt. %, or about 44.0 wt. % Ti.

The powder 210 may comprise trace elements such as any one or more of: C, Co, Cu, Cr, H, Fe, Nb, N, and O. In some embodiments, the powder 210 comprises no more than about 0.05 wt. % of each of C, Co, Fe, and N+O (nitrogen and oxygen being measured together). In some embodiments, the powder 210 comprises no more than about 0.025 wt. % of Nb. In some embodiments, the powder 210 comprises no more than about 0.01 wt. % of each of Cu and Cr. In some embodiments, the powder 210 comprises: <4.8 ppm Co, <3 ppm Cu, <2 ppm Cr, <86.5 Fe, and <3 ppm Nb. The chemical composition may be determined using techniques such as atomic emission spectroscopy, for example, inductively charged plasma optical emission spectroscopy (ICP-OES). Light interstitial elements such as C, N and O may be measured using inert gas fusion, infrared absorption or thermal conductivity measurements, for example with equipment provided by LECO.

In some embodiments, the powder 210 comprises no more than about 0.035 wt. % of each of C, Fe, and N+O. The powder 210 may comprises no more than about 0.01 wt. % of each of Co, Cr. The powder 210 may comprise no more than about 0.002 wt. % of each of Cu, H and Nb. For example, the powder 210 may comprise: 0.034 wt. % C, 0.01 wt. % Co, 0.001 wt. % Cu, 0.004 wt. % Cr, <0.001 wt. % H, 0.023 wt. % Fe, <0.002 wt. % Nb, and 0.021 wt. % N+O. The powder 210 may, for example, be supplied by Advanced Powders & Coatings (AP&C), Canada. The powder 210 may be in accordance with ASTM F2063.

Figures 4A, 4B, 4C, 4D:
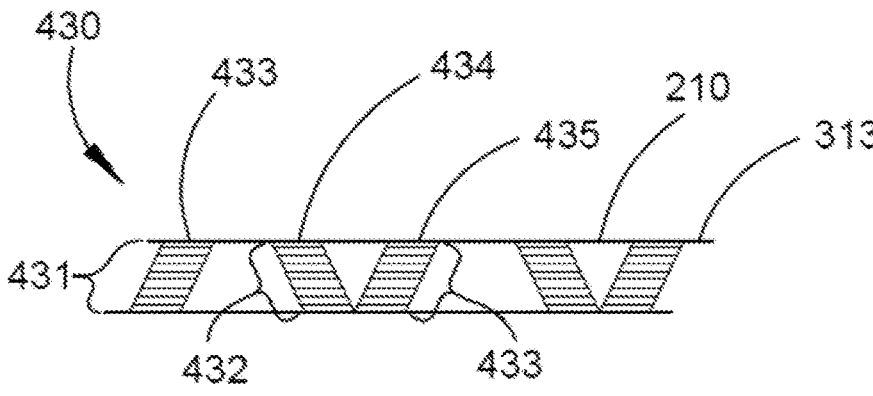
FIG. 4(a) is a side view of a plurality of stacked layers.
FIG. 4(b) is a top view of the plurality of stacked layers of FIG. 4(a).
FIG. 4(c) is a side view of an implantable object comprising struts.
FIG. 4(d) is a top view of the implantable object of FIG. 4(c)

Referring to FIGS. 4(*a*) to 4(*d*), the plurality of stacked layers 430 may comprise more than one group of stacked layers 431, 432, 433. Each group of stacked layers 430 may form a component 401, 402, 403 of the implantable object 300, 400. During fabrication each some of the groups of stacked layers 432, 433 may be directly connected to each other while some groups 431 may not be directly connected (i.e. they may be separated by intervening powder 210). Each layer at a particular height along the third axis Z may therefore comprise a plurality of isolated solid areas 434, 435, 433.

In some embodiments, the isolated solid areas 433, 434, 435 may be formed by changing the relative position over a curved track such as a circular track. The curved track may, for example, follow the curve of the circumference of the isolated solid areas 434, 435, 433. The energy source 220 may be selectively switched on and off as the relative position changes to produce the isolated solid areas 434, 435, 433. The length of solid areas 434, 435, 436 is thereby determined by the speed that the relative position changes and the duration that the energy source 220 is applied for. The isolated solid areas 434, 435, 433 may be formed by a single curved track if the dimensions of melt area (transverse to the direction the position changes along the curved track) are similar to the desired dimensions of the solid areas 434, 435, 433.

In some embodiments, the outer periphery (not shown) of the isolated solid areas 434, 435, 433 may be formed by changing the relative position over a curved track such as a circular track. The internal area (not shown) of the isolated solid areas 434, 435, 433 may be formed by either iteratively changing the relative position over one or both of the first axis X and second axis Y over any one or more of a plurality of linear tracks, a spiral track, and/or curved tracks.

Fabrication parameters such as laser power, scan speed, layer thickness T and hatch spacing H may affect the energy density delivered by the laser to the powder surface 313. However, the microstructure and mechanical properties may not be the same for metallic objects fabricated using additive manufacturing with different combinations of parameters but the same energy density. Therefore, extrapolating and/or interpolating from previous results may not enable prediction of the microstructure and/or mechanical properties of metallic objects fabricated with additive manufacturing.

The laser beam may have a power in the range of about 55 W to less than 200 W (e.g. about 195 W). In some embodiments, the power is in the range of about 75 W to about 125 W. In some embodiments, the power is about 75 W (low power). In some embodiments, the power is about 125 W (high power).

As mentioned, the energy density of the laser beam at the powder surface 313 is affected by, among other parameters, the scan speed. For the above laser power range, the scan speed may be in the range of about 100 mm/s to 2000 mm/s to provide an adequate energy density. In some embodiments, where a low laser power is used, the scan speed may be in the range of 100 mm/s to 1000 mm/s. The appropriate scan speed will depend on the dimensions of the features being fabricated, with higher scan speeds used for finer features.

For a laser beam with a high power of 125 W, the scan speed may be greater than about 600 mm/s. In some embodiments, for a high power laser beam, the scan speed may be in the range of about 600 mm/s to 1200 mm/s.

In some embodiments, for a high power laser beam, the hatch spacing H may be in the range of about 70 microns to about 110 microns. For example, the hatch spacing H may be either 75 microns or 100 microns.

In some embodiments, the steps of melting a powder 110 and iterative forming 120 stacked metallic layers 330 may be defined by parameters. The parameters may comprise any one or more of: the laser beam power, the hatch spacing H, powder layer thickness and the scan speed. The parameters may be selected to produce an energy density less than about 90 kJ/mm³. The parameters may be selected to produce an energy density less than about 75 kJ/mm³. The parameters may be selected to produce an energy density in the range of about 50 kJ/mm³ to about 75 kJ/mm³. Minimising the energy density may reduce the amount of Ni evaporation during iteratively forming the stacked layers 330. For example, iteratively forming the stacked metallic layers 330 with a hatch spacing greater than 50 microns may result in an implantable object 300, 400 with greater than or equal to about 54.1 wt. % nickel.

Figure 5:
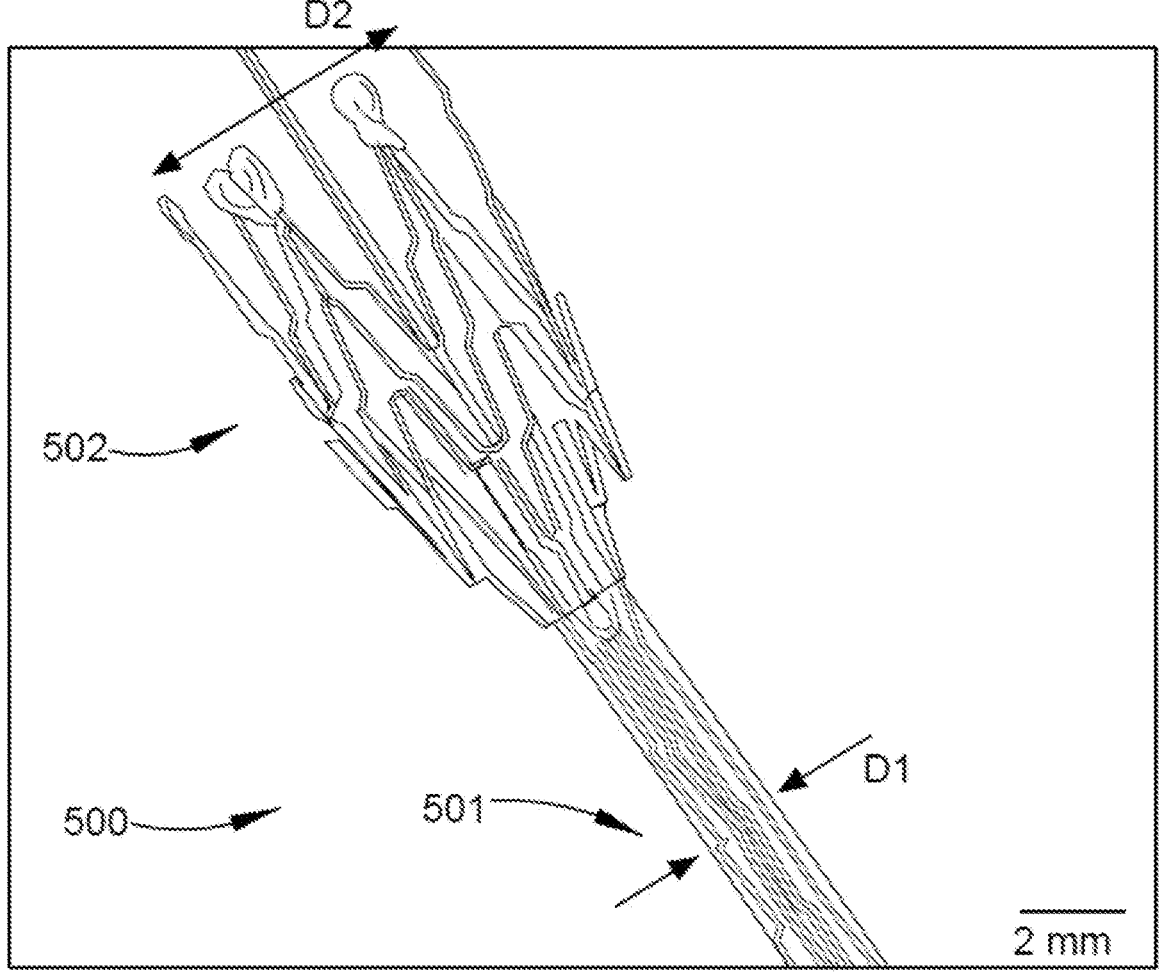
FIG. 5 is an optical image of an implantable object with one portion in a contracted first configuration and another portion in an expanded second configuration.

In some embodiments, the method 100 may comprise fabricating an implantable object 500 of FIG. 5. Object 500 is capable of self-expanding from a first configuration 501 (contracted configuration) to a second configuration 502 (expanded configuration) when the implantable object 300, 400, 500 is heated to or above a transformation temperature.

FIG. 5 shows a commercially available stent exemplifying portions in the first configuration 501 and the second configuration 502. While the implantable object 300, 400, 500 shown in FIG. 5 has one portion that is in a first configuration 501 and another portion that is in a second configuration 502, in some embodiments, the implantable object 300, 400, 500 may be completely in either: the first configuration 501, or the second configuration 502.

The implantable object 300, 400, 500 may be a stent. The stent may define a first diameter D1 in the first configuration that is smaller than a second diameter D2 in the second configuration. The first diameter D1 and second diameter D2 being measured across a lateral cross-section of the implantable object 300, 400, 500.

The implantable object 300, 400, 500 may be formed from a biocompatible material such as nitinol. The implantable object 300, 400, 500 may be sized or configured such that it is suitable for implantation into a human body. For example the implantable object 300, 400, 500 may form part of a stent, a bone implant, or a bone replacement.

The implantable object 300, 400, 500 may, for example, be a vascular stent such as a coronary stent or a peripheral stent. The implantable object 300, 400, 500 may be compressed prior to implantation into a human body (not shown) such that it can be inserted into an applicator (not shown) such as a catheter (not shown). The applicator may be used to implant the implantable object 300, 400, 500 into a blood vessel (not shown) such as a coronary artery of the human body. Once the implantable object 300, 400, 500 is heated above its transformation temperature (such as during or after implantation into a blood vessel) the implantable object 300, 400, 500 can self-expand within the blood vessel.

In some embodiments, the implantable object 300, 400, 500 is sized to be implanted into a body such as a human body.

The fabricated implantable object 300, 400, 500 may be defined by a transformation temperature. The transformation temperature may, for example, be a finish temperature at which the martensitic phase of Ni—Ti intermetallic regions within the implanted object 300, 400, 500 finishes transforming to the austenitic phase. The austenite finish temperature is abbreviated as $A_f$.

The fabricated implantable object 300, 400, 500 may therefore comprise a superelastic alloy that is shaped and/or configured such that the implantable object 300, 400, 500 expands from a contracted (first) configuration (expands in overall size) when heated to or above the transformation temperature. The fabricated implantable object 300, 400, 500 or at least some components of the implantable object 300, 400, 500 may also exhibit shape memory properties when at the transformation temperature or above the transformation temperature.

In some embodiments, the finish temperature is less than or at about human body temperature. For example, the finish temperature may be less than about 36° C. The finish temperature may be less than about 36.5° C. Finish temperatures below human body temperature enables the implanted object 300, 400, 500 to comprise austenitic phases and minimal or negligible amounts of martensitic phases when implanted into a human body.

The implantable object 300, 400, 500 may exhibit superelastic properties when at a temperature above the austenite finish temperature, $A_f$. As a result of the superelastic properties, the implantable object 300, 400, 500 may be compressed into the contracted configuration without excessive damage (such as fracturing or cracking). When in the contracted configuration, the implantable object 300, 400, 500 may be shaped and configured such that it is biased to expand into the expanded configuration as a result of its superelastic properties.

The implantable object 300, 400, 500 may be compressed into the contracted configuration below the finish temperature. When the implantable object 300, 400, 500 is in the contracted configuration, it may be loaded or inserted into a catheter or implantation device which may constrain the implantable object 300, 400, 500 in the contracted configuration. This may enable the implantable object 300, 400, 500 to be implanted into the body while in the contracted configuration. The implantable object 300, 400, 500 may expand or be expandable to an expanded configuration within the human body when it is heated to body temperature.

The finish temperature may also be greater than or at about room temperature. The finish temperature may, for example be greater than or at about 21° C. The finish temperature may, for example be greater than or at about 24° C.

The build parameters such as laser power, scan speed, layer thickness T and hatch spacing H may affect the transformation temperature. For example, fabrication of the implantable object 300, 400, 500 may cause excessive nickel evaporation and lead to an implantable object 300, 400, 500 that has a nickel concentration of less than 54.5 wt. %. A reduction of about 1 wt. % of nickel may result in an increase in transformation temperature of up to 100° C. For example, a nickel concentration of less than about 54.1 wt. % may lead to a transformation temperature that is higher than 36° C.

The elemental composition of the implantable object 300, 400, 500 may be determined using energy dispersive X-ray spectroscopy (EDS), for example, in a scanning electron microscope (SEM). Alternatively, a sample of the implantable object 300, 400, 500 may be obtained and analysed with optical emission spectroscopy (ICP-OES) to determine the elemental composition of the implantable object 300, 400, 500.

The build parameters may be selected to fabricate the implantable object 300, 400, 500 such that the nickel concentration of the implantable object 300, 400, 500 is at least 54.1 wt. %. The build parameters may be selected to fabricate the implantable object 300, 400, 500 such that the nickel concentration of the implantable object 300, 400, 500 is at least 54.5 wt. %.

In an embodiment, the build parameters comprise: a laser power of 125 W, a powder layer thickness T of 30 microns, a hatch spacing of 75 microns, and a scanning speed in the range of about 800 mm/s to about 900 mm/s. These build parameters result in a calculated energy density between about 60 kJ/mm³ to about 70 kJ/mm³. Fabricating an implanted object 300, 600 with these build parameters using a powder 210 with a nickel concentration of about 54.5 wt. % may result in an implanted object 300, 600 with a nickel concentration of about 54.4 wt %. In these embodiments, with a scanning speed of about 800 mm/s the austenite finish temperature, $A_f$, may be about 16° C. (as-fabricated). For a scanning speed of about 900 mm/s the martensite-to-austenite finish temperature may be about 6° C. (as-fabricated).

In some embodiments, the build parameters comprise: a laser power of 125 W, a powder layer thickness T of 30 microns, a hatch spacing of 100 microns, and a scanning speed in the range of about 600 mm/s to about 700 mm/s. These build parameters result in a calculated energy density between about 60 kJ/mm³ to about 70 kJ/mm³. Fabricating an implanted object 300, 600 with these build parameters using a powder 210 with a nickel concentration of about 54.5 wt. % may result in an implanted object 300, 600 with a nickel concentration of about 54.2 wt %. In these embodiments, with a scanning speed of about 600 mm/s the austenite finish temperature, $A_f$, may be about 14° C. For a scanning speed of about 700 mm/s austenite finish temperature, $A_f$, may be about 5° C.

The implantable object 300, 400, 500 may also comprise an area fraction of non-metallic inclusions that is less than about 3%. The non-metallic inclusions may, for example, comprise Ti, O and C. In some embodiments, the implantable object 300, 400, 500 comprises an area fraction of non-metallic inclusions that is less than about 2.8% and therefore in accordance with ASTM F2063. The implantable object 300, 400, 500 may comprise an area fraction of non-metallic inclusions that is less than about 0.5%. The area fraction of non-metallic inclusions may be determined from analysis of SEM images/micrographs.

Figure 6:
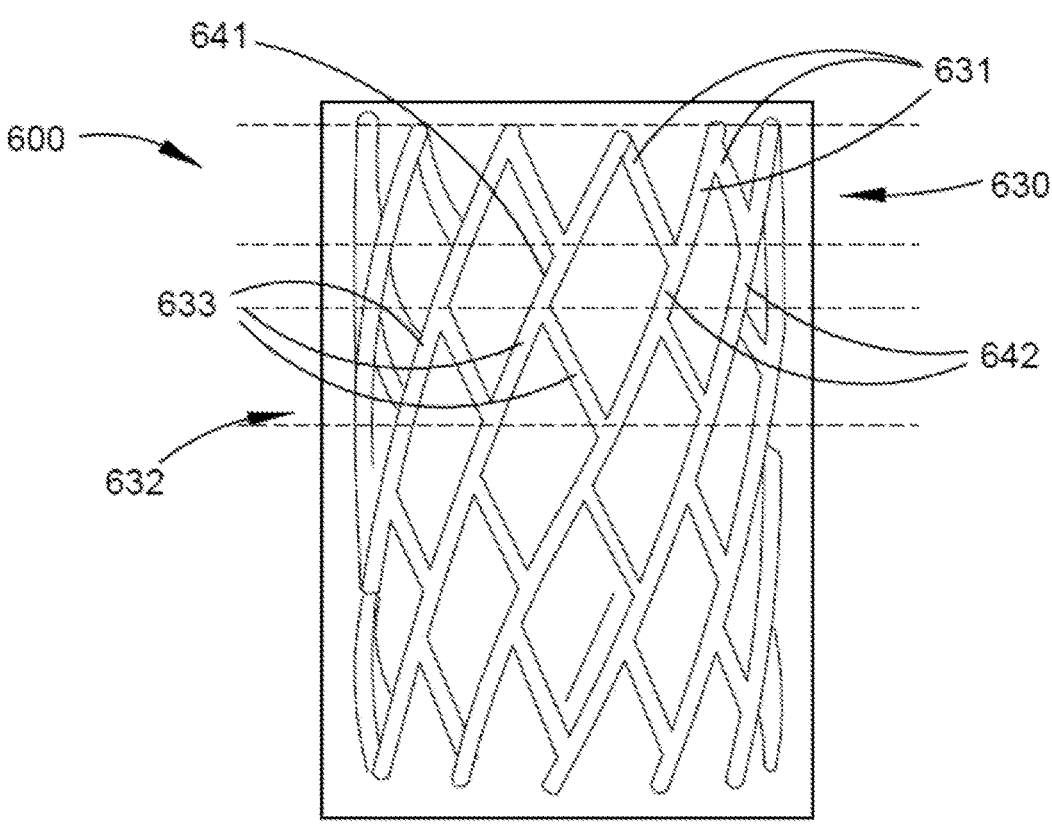
FIG. 6 is a side view illustration of an as-built stent formed by additive manufacturing.
Figure 7:
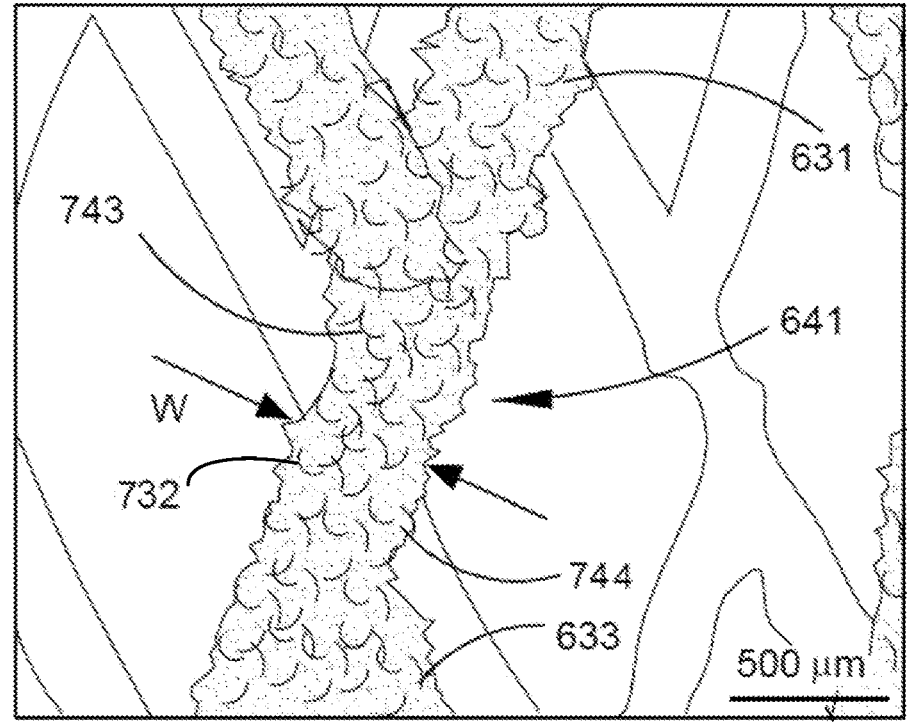
FIG. 7 is an illustration of a section of the as-built stent of FIG. 6.

Referring to FIGS. 6 and 7, the implantable object 300, 400, 500, 600 may comprise a plurality of crowns 630, 632. Each crown 630, 632 may comprise a plurality of connected struts 631, 633 formed by additive manufacturing. Subsets of the struts 631, 633 may form V- or Y-shaped structures and provide connecting elements such as bridges, hinges or nodes between other struts 631.

A first crown 630 may be attached to a second crown 632 via at least one first bridging strut 641. The first crown 630 may also be attached to the second crown 632 via at least one sacrificial strut 642 which is also a type of bridging strut. Sacrificial strut 642 is not present in the final object 300, 400, 500, 600 and is created to provide support to other struts or features during the additive manufacturing process. Sacrificial strut 642 is thinner than other bridging struts 641 and is later removed during step 140, as described in detail below.

Referring to FIG. 7, the bridging struts 641, 642 comprise a first end 743 opposite to a second end 744. The first end 743 may be attached to a strut 631 on a first crown 630 and the second end 744 may be attached to another strut 633 on a second crown 632. The surface of the struts may comprise a plurality of particles 732 attached to the surface. The particles 732 may comprise one or more individual particles from the powder 210 which may only have been partially melted during additive manufacturing.

The dimension W of the struts 641, 642 may be defined by a lateral width perpendicular to a longitudinal length of the struts 641, 642. In some embodiments, the thickness W of the first bridging struts 641 may be greater than the thickness W of the second bridging struts 642. The thickness W of the first bridging struts 641 may be the same as the thickness of the connected struts 631, 633. A first set of struts may comprise the first bridging struts 641 the connected struts 631, 633. The thickness W of the first set of struts may therefore be greater than the thickness W of the second set of struts 642.

The thickness W of the first set of struts 631, 633 and/or bridging struts 641 may be in the range of about 150 microns to about 300 microns. The thickness W of the first set of struts 631, 633 and/or bridging struts 641 may, for example, be about 200 microns.

In some embodiments, the thickness W of the first set of struts 631, 633 and/or bridging struts 641 is in the range of about 300 microns to about 500 microns. The thickness W of the first set of struts 631, 633 and/or bridging struts 641 may be in the range of about 350 microns to about 450 microns.

The thickness W of the second set of bridging struts 642 may be in the range of about 150 microns to about 250 microns. The thickness W of the second set of bridging struts 642 may be less than about 250 microns. The thickness W of the second set of bridging struts 642 may be about 200 microns.

The second set of bridging struts 642 may provide support for the implantable object 500, 600 during fabrication of the implantable object 500, 600. As a result, an additional mandrel and/or separate support structure may not be necessary to produce the implantable object 500, 600 with additive manufacturing.

Figure 10:
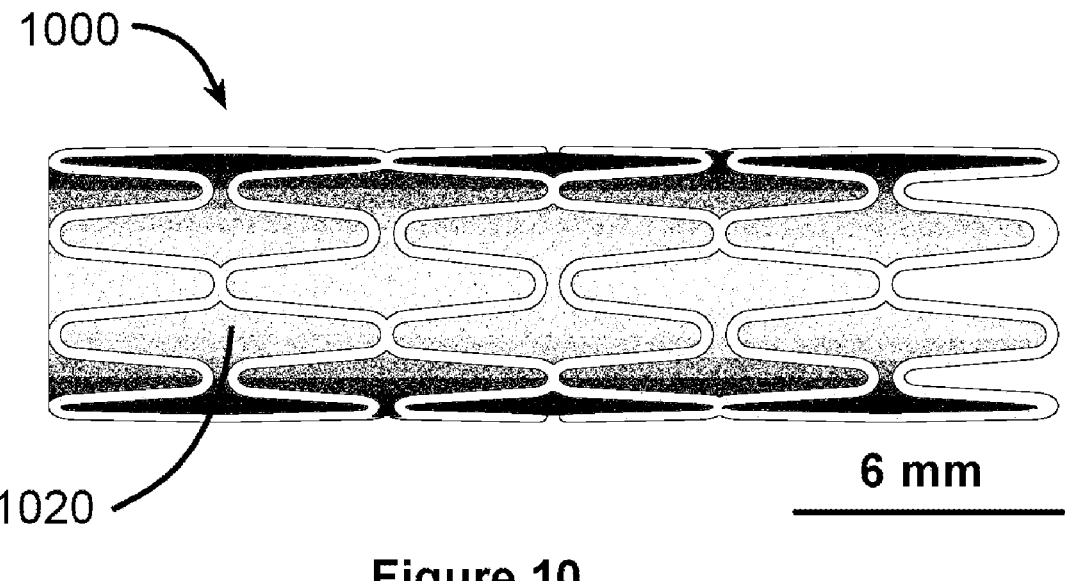
FIG. 10 is an illustration of a stent having a support surface.

In some embodiments, sacrificial struts 642 are not used during additive manufacturing. Rather, a sacrificial support surface is created. An example of a stent 1000, including sacrificial support surface 1020, is shown in FIG. 10. Sacrificial support surface 1020 is porous and of a lower density in comparison to the object and is formed as part of the same manufacturing process as the object.

As mentioned above, a sufficient energy density, provided by the laser, is required to achieve proper powder fusion. Furthermore, the energy density delivered to the powder is affected by the speed at which the laser is scanned over the powder. If insufficient energy density is delivered to the powder, partly fused powder particles result, creating a low density porous structure. The embodiment utilising the sacrificial support surface takes advantage of these observations. That is, the manufacturing parameters are altered to deliver an insufficient energy density to the powder in sections where a sacrificial support surface is desired while sufficient energy density is delivered to sections which will be part of the finished object.

For example, dense stent struts can be fabricated using a laser power of 75 W and a scan speed of about 800 mm/s. These parameters, as described above, ensure that an adequate energy density is delivered to the powder to properly fuse it. To produce support surface 1020, the laser scan speed can be increased, thereby reducing the energy density delivered to the powder. The lower energy density causes partial fusion of the powder, resulting in a low density, porous structure which can be removed during surface treatment (described below). For example, the scan speed can be increased to 1200 mm/s, which causes partial fusion of powder 210. The support surface 1020 can be used to support structures that are not yet connected or sufficiently supported until the final object 1000 is completed. For example, parts of the object that are inclined (<45° to the build plate) or overhanging (parallel to the build plate). These support surfaces 1020 may also function as anchors, dissipate heat and prevent thermal warping of the parts.

Figure 11:
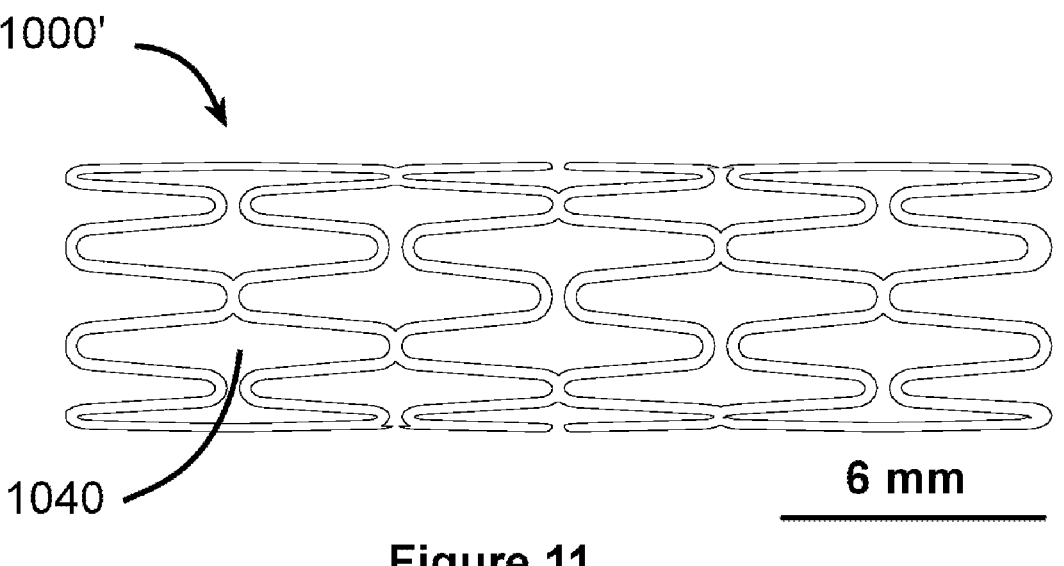
FIG. 11 is an illustration of the stent of FIG. 10 with the support surface removed.

FIG. 11 illustrates stent 1000' which is stent 1000 after support surfaces 1020 have been removed by a surface treatment regimen as described in detail below. Support surfaces 1020 are replaced by vacant spaces 1040. In brief, the surface treatment regimen involves dissolving support surfaces 1020 by pickling and electro-polishing. Note that the surface treatment also reduces the size of the struts in stent 1000' in comparison to those in stent 1000.

Heat Treatment

In some embodiments, method 100 further comprises heat treating the implantable object 300, 400, 500 in an inert atmosphere, at 130. The heat treatment 130 may comprise heating the implantable object 300, 400, 500 to a set temperature in the range of about 800° C. to about 1000° C., referred to as solution heat treatment, and may further comprise an ageing heat treatment step. The ageing heat treatment step is conducted at lower temperatures, in the range 300-550° C. for durations of between 2 and 30 minutes, followed by water quenching. It was found that the appropriate heat treatment depended on the dimensions of the implantable object 300, 400, 500.

For example, for cuboid objects of 8 to 10 mm in each dimension, the heat treatment 130 may comprise heating the implantable object 300, 400, 500 to a temperature of about 1000° C., for solution heat treatment. The heat treatment 130 may, comprise heating the implantable object 300, 400, 500 to a temperature of about 800° C. for solution heat treatment. The heat treatment 130 may, comprise heating the implantable object 300, 400, 500 to a temperature of about 950° C. for solution heat treatment. The heat treatment 130 may comprise heating the implantable object 300, 400, 500 to a set temperature in the range of about 800° C. to about 980° C. solution heat treatment. The heat treatment 130 may comprise heating the implantable object 300, 400, 500 to a set temperature in the range of about 800° C. to about 950° C. for solution heat treatment.

The heat treatment 130 may comprise placing the implantable object 300, 400, 500 into a furnace such as a vacuum furnace or muffle furnace.

The solution heat treatment step of 130 may homogenise the microstructure of the fabricated implantable object 300, 400, 500 so that it has a more uniform distribution of nickel. The solution heat treatment may lower the transformation temperature of the implantable object 300, 400, 500. Therefore, build parameters that result in an as-fabricated object with a transformation temperature higher than desired may be used in combination with the heat treatment 130 to thereby lower the transformation temperature of the implantable object 300, 400, 500 to or below the desired temperature.

The heat treatment 130 may comprise subjecting the implantable object 300, 400, 500 to the set solution heat treatment temperature for a duration in the range of about 30 minutes to about 3 hours. In some embodiments, the solution heat treatment comprises subjecting the implantable object 300, 400, 500 to the set temperature for about 2 hours.

In some embodiments, the heat treatment 130 is followed by quenching the implantable object 300, 400, 500 into a liquid such as water. The water may be at room temperature. In some embodiments, the liquid may have been cooled by ice and therefore be at a temperature of about 0° C. Quenching the implantable object 300, 400, 500 may, for example, limit precipitation of unwanted phases in the implantable object 300, 400, 500. However, during and/or after quenching an oxide layer may also form on surfaces of the implantable object 300, 400, 500 exposed to the liquid.

In some embodiments, the inert atmosphere is a low oxygen environment. The low oxygen environment limits or prevents oxide growth during the heat treatment 130. The implantable object 300, 400, 500 may, for example, be placed into an evacuated container such as a quartz tube (not shown). The quartz tube may be evacuated and backfilled with an inert gas such as Ar. The step of evacuating and backfilling may be repeated a plurality of times, for example at least 6 times. The heat treatment 130 may comprise placing the implantable object 300, 400, 500 in a vacuum furnace. The vacuum furnace may, for example, be a tube furnace. In some embodiments, the heat treatment 130 may comprise placing the implantable object 300, 400, 500 in an environment with a flowing inert gas such as Ar.

In an example, the build parameters may comprise: a laser power of 125 W, a powder layer thickness T of 30 microns, a hatch spacing of 75 microns, and a scanning speed in the range of about 600 mm/s, the austenite finish temperature, $A_f$, may be about 24° C. in an as-fabricated implantable object 300, 400, 500. However, heat treating at about 1000° C. for about 2 hours in a low-oxygen Ar environment and quenching in water may lower the austenite finish temperature, $A_f$, to about –3° C.

In an example, the build parameters may comprise: a laser power of 125 W, a powder layer thickness T of 30 microns, a hatch spacing of 50 microns, and a scanning speed in the range of about 800 mm/s, the austenite finish temperature, $A_f$, may be about 24° C. in an as-fabricated implantable object 300, 400, 500. However, heat treating at about 1000° C. for about 2 hours in a low-oxygen Ar environment and quenching in water may lower the austenite finish temperature, $A_f$, to about –3° C.

For objects with dimensions of 200 to 400 μm, an appropriate heat treatment comprises a solution heat treatment of the item at 800° C. for 30 minutes, followed by water quenching and an ageing heat treatment and a second water quenching.

The austenite finish temperature, $A_f$, after the solution heat treatment is approximately –18.3° C. Higher temperatures for the solution heat treatment results in lower $A_f$ temperatures. For example, a solution heat treatment temperature of 850° C. for 30 minutes results in an $A_f$ temperature of –28.8° C. while a solution heat treatment temperature of 900° C. for 30 minutes results in an $A_f$ temperature of –29.1° C.

As mentioned, an ageing heat treatment is then performed on the item. The ageing heat treatment causes precipitation of $Ni_4Ti_3$ phases which adjusts the austenite finishing temperature. An ageing heat treatment of 450° C. for 5 minutes, followed by water quenching, adjusts the $A_f$ from –18.3° C. to 19.5° C. The final $A_f$ after the ageing heat treatment can be adjusted by changing the ageing heat treatment temperature and time. For example, an ageing heat treatment at 450° C. for 10 minutes results in an $A_f$ of 17.2° C. while an ageing heat treatment at 450° C. for 15 minutes results in an $A_f$ of 23.5° C. Similarly, an ageing heat treatment at 400° C. for 15 minutes results in an $A_f$ of 36.7° C. and an ageing heat treatment at 450° C. for 15 minutes results in an $A_f$ of 34.4° C.

Surface Treatment

In some embodiments, the method 100 further comprises removing at least a portion of the plurality of struts 631, 633 and/or bridging struts 641, 642, at 140. Removing at least a portion of the struts 631, 633 and/or bridging struts 641, 642 may reduce the thickness W. The thickness W may, for example, be reduced to less than about 200 microns.

The thickness W may be reduced by about 50% as a result of the reducing step 140. The thickness W may be reduced by an amount in the range of about 100 microns to about 200 microns as a result of the reducing step 140. For example, a fabricated stent 500, 600 may comprise struts 631, 632 with an as-fabricated thickness W of about 400 microns but the thickness W is reduced to about 200 microns following the reducing step 140.

Figure 9:
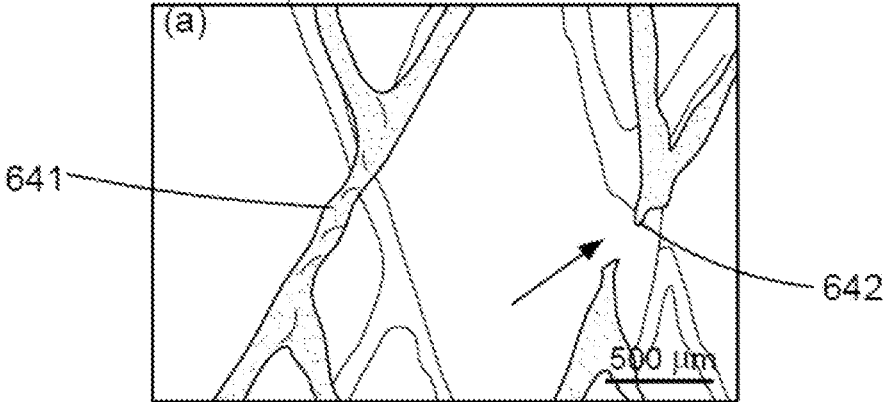
FIG. 9 is an illustration of struts from an implantable object formed by additive manufacturing after partial removal of some of the struts.

The reducing step may comprise initially removing at least part of the bridging struts 642 (see FIG. 9). The method 100 may also comprise completely removing the second set of bridging struts 642 to enable the implantable object 500, 600 to be used as a stent. This is particularly advantageous for the fabrication of stents with an open-cell design. The second set of bridging struts 642 may therefore be considered as sacrificial support structures.

The step 140 of removing at least a portion of the struts 631 and/or bridging struts 641, 642 may comprise removing at least a portion of a surface of the implantable object 300,

400, 500, 600 (or at least some the struts 631 and/or bridging struts 641, 642). The removing step 140 may comprise, for example, any one or more of: chemical etching, acid pickling, micro-abrasive blasting, and electro-polishing.

As shown in FIG. and 7, the surface of an as-fabricated implantable object 300, 400, 500, 600 may be rough and comprise a plurality of particles 732 attached to the surface. The particles 732 may comprise one or more individual particles from the powder 210 which may only have been partially melted during additive manufacturing.

Figure 8:
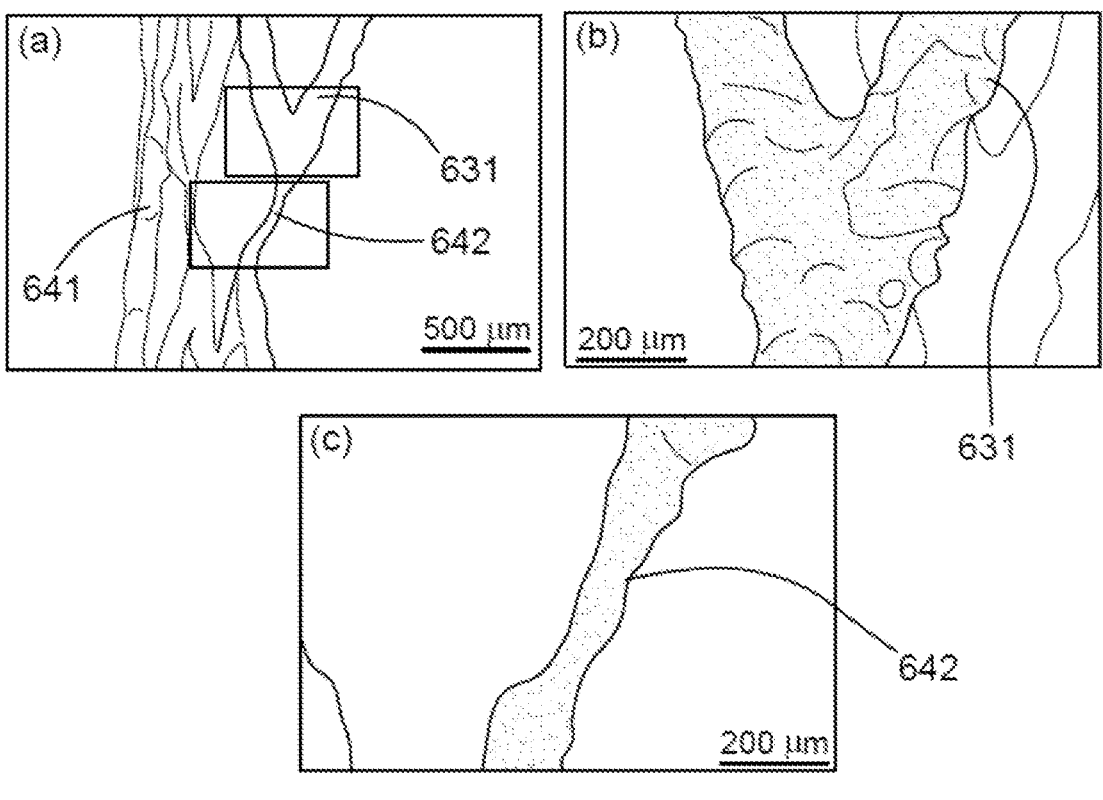
FIG. 8(a) is an illustration of a stent formed by additive manufacturing after some of the surface of the struts have been removed.
FIG. 8(b) shows a magnified view of the top inset rectangle in FIG. 8(a)
FIG. 8(c) shows a magnified view of the bottom inset rectangle in FIG. 8(a)

FIGS. 8(*a*) to 8(*c*) and 9 illustrate parts of the implantable object after reducing step 140 which may result in removal of at least the particles 732 attached to the surface of the implantable object 300, 400, 500, 600. The reducing step 140 may also remove any surface oxide that formed during either fabrication 120 or heat treatment 130. The reducing step 140 may be a surface treatment.

Acid pickling may comprise exposing the surface of the struts 631 and/or bridging struts 641, 642 to an acid solution (acid etching or polishing). The acid solution may comprise any one or more of HF, $HNO_3$, $H_2O$ and $H_2SO_4$. In some embodiments, the acid solution comprises HF, $HNO_3$, and $H_2O$ in a ratio of about 1:2:3. In some embodiments, the acid solution comprises HF, $H_2SO_4$, and $H_2O$ in a ratio of about 1:4:5.

The duration that the implantable object 300, 400, 500, 600 is exposed to the acid solution may determine how much the thickness W of the struts 631, 633, 641, 642 is reduced. The duration of exposure to the acid solution may be in the range of about 1 minute to about 40 minutes. The duration of exposure to acid solution may, for example, be about 10 minutes, about 20 minutes or about 30 minutes.

In some embodiments, the exposure to the acid solution is performed in time intervals. This allows for an optional rinsing and/or cleaning step (e.g. ultrasonic cleaning, rinsing in water) between being exposed to the acid solution. For example, referring to FIG. 8, the reducing step 140 may comprise acid pickling with a solution of HF, $HNO_3$, and $H_2O$ in a ratio of about 1:2:3 for intervals of 10 minutes for a total duration of 40 minutes, where the implantable object 300, 400, 500, 600 is ultrasonically cleaned between acid pickling intervals. The thickness W of strut 631, 633, 641 may be reduced by about 120 microns to about 200 microns.

Micro-abrasive blasting (or micro-girt blasting) comprises mixing micron sized abrasive particles with dry air. The abrasive particles may comprise alumina or glass beads. This mixture is then propelled out of a small nozzle tip at high velocity and focused into an abrasive stream. In some embodiments, a nozzle tip with a diameter of about 0.5 mm is used. Without masking or shielding, blasting can be restricted to very small areas.

Electro-polishing may comprise exposing the implantable object 300, 400, 500, 600 to a 10% solution of $H_2SO_4$ and methanol. In some embodiments, a voltage of at least 3 V may be applied. A voltage of about 8V may be applied to the implantable object 300, 400, 500, 600 acting as an anode and a stainless steel component acting as a cathode for about 2 minutes.

In some embodiments, the reducing step 140 may comprise a combination of acid pickling and electro-polishing. The reducing step 140 may comprise acid pickling followed by electro-polishing. For example, acid pickling in $HF/HNO_3/H_2O$ (ratio of 1:2:3) for total of 40 min may reduce the thickness W of struts 631, 633, 641, by about 130 microns (FIG. 8). Further electro-polishing in 10% $H_2SO_4$ in methanol at 8 V for about 2 minutes may reduce the thickness W of struts by about another 80 microns. As an example, the thickness W of struts 631, 633, and 641 may therefore be reduced from about 400 microns to about 190 microns. Sacrificial struts 642 are dissolved away during this step as shown in FIG. 9.

Electro-polishing in 10% $H_2SO_4$ in methanol at 8 V for about 3 min after acid pickling may reduce the thickness W of struts by about 130 microns. Therefore, in combination with acid pickling in $HF/HNO_3/H_2O$ in the ratio of 1:2:3 for 40 min, the thickness W of struts 631, 632, and 641 may be reduced from about 400 microns to about 140 microns (FIG. 9).

An alternative pickling solution may comprise 5% HF+30% $HNO_3$ in water. The exact pickling time will depend on the dimensions of object. For example, for stent struts of the dimensions discussed herein, typical pickling times are between 15 and 30 minutes.

Unless actively cooled, the electrolyte temperature increases during the electro-polishing step. As the flash point for methanol is only around 26° C., the electro-polishing procedure outlined above requires active cooling. To overcome the requirement for active cooling, an alternative electro-polishing procedure was developed. In this procedure, electro-polishing was performed using 100% methanesulfonic acid as the electrolyte. Methanesulfonic acid has a flash point above 170° C. making it a safe electrolyte to use for electro-polishing at standard laboratory temperatures without a need for active cooling.

The time and voltage at which the electro-polishing is carried out is specific to a given item being fabricated, with finer structures requiring shorter electro-polishing times. Voltages in the range of 10 to 25 V are typical and polishing times in the range 10-40 minutes are typical, at temperatures in the range 20-30° C.

In some embodiments, the reducing step 140 may reduce the thickness W of struts 631, 633, 641 to a thickness in the range of about 80 microns to about 140 microns by at least one of acid pickling and electro-polishing.

A set of computer-readable instructions may be stored on a storage device (not shown) such as a non-volatile medium. The instructions when executed by a processor not shown) enables additive manufacturing equipment to implement method 100. The storage device may also store a data file that encodes a design for the implantable object 400, 500, 600. The data file may, for example, comprise a computer aided design (CAD) file. The data file may comprise the build parameters.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of fabricating a stent comprising:

forming one or more stent struts by:

melting a powder comprising at least nickel and titanium by delivering energy to the powder at a first energy density from an energy source; and iteratively forming a plurality of stacked metallic layers from the melted powder using additive manufacturing; and forming a support surface by:

partially fusing the powder by delivering energy to the powder at a second energy density from the energy source, wherein the second energy density is lower than the first energy density from the energy source; and iteratively forming a plurality of stacked support layers wherein each support layer is formed from the partially fused powder using the additive manufacturing, wherein the support surface has a porous structure and is formed as one or more sacrificial sections interleaved between adjacent ones of the one or more stent struts, the one or more sacrificial sections being configured to support the one or more stent struts during the fabrication of the stent and to be removed by a surface treatment that dissolves the support surface, such that the stent is biased to expand from a first configuration to a second configuration when at or above a phase transformation temperature.

2. The method of claim 1 further comprising removing the support surface following forming the one or more stent struts.

3. The method of claim 1, wherein iteratively forming the stacked metallic layers and the stacked support layers comprises iteratively changing a position of the energy source along a first axis and then the position changes along a second axis parallel to the first axis with a hatch spacing between the first axis and second axis in the range of 30 microns to 100 microns.

4. The method of claim 3, wherein the position changes with a speed in the range of 105 mm/s to 1245 mm/s.

5. The method of claim 1, wherein the energy source is a laser beam with a power in the range of 55 W to less than 200 W, wherein a hatch spacing, a scan speed, and the power of the laser beam are selected to produce the first energy density in the range of 50 $KJ/mm^3$ to 90 $KJ/mm^3$.

6. The method of claim 1, wherein melting the powder is performed while the powder is supported by a nickel-titanium alloy substrate.

7. The method of claim 1, wherein the energy source is focused on the powder to produce molten powder such that the molten powder has a lateral dimension in the range of 75 microns to 200 microns.

8. The method of claim 1, wherein the iterative forming of stacked layers comprises forming at least one layer of molten powder with a thickness in the range of 20 microns to 40 microns.

9. The method of claim 1, wherein the transformation temperature is a finish temperature, $A_{fi}$ for transformation from martensite to austenite, wherein the $A_f$ temperature is less than or at human body temperature.

10. The method of claim 1, wherein the powder comprises at least 56 weight % nickel.

11. The method of claim 1, wherein the stent is formed from a shape memory alloy and/or is superelastic when above the $A_f$ transformation temperature.

12. The method of claim 1 further comprising pickling the stent in a solution comprising hydrofluoric acid (HF) and nitric acid ($HNO_3$) for a predetermined time period, and wherein the predetermined time period is 15 minutes and the solution comprises 5% HF, 30% $HNO_3$ and 65% water.

13. The method of claim 1 further comprising electro-polishing the stent in a solution of sulphuric acid ($H_2SO_4$) and methanol, wherein the solution comprises 10% sulphuric acid and the electro-polishing is performed at a voltage of 8 V.

14. The method of claim 1 further comprising electro-polishing the stent in methanesulfonic acid, and wherein the electro-polishing is performed at a voltage of 20 V.

15. The method of claim 2, wherein the support surface is removed by applying a surface treatment to dissolve at least the support surface.

16. The method of claim 1, wherein the support surface is configured to anchor, or to dissipate heat from, the one or more stent struts during the additive manufacturing.

17. The method of claim 3, wherein the energy is delivered to the powder at a constant power from the energy source as the position of the energy source changes, and wherein a rate of change of the position of the energy source is increased to form the plurality of stacked support layers, compared to a rate of change of the position of the energy source to form the plurality of stacked metallic layers.

* * * * *